(12) United States Patent
Pirker

(10) Patent No.: US 8,601,881 B2
(45) Date of Patent: Dec. 10, 2013

(54) MATERIAL SAMPLE FOR TESTING BIAXIAL STRESS CONDITIONS

(75) Inventor: Klaus Pirker, St. Lambert (CA)

(73) Assignee: MTU Aero Engines GmbH, Munich (DE)

( * ) Notice: Subject to any disclaimer, the term of this patent is extended or adjusted under 35 U.S.C. 154(b) by 232 days.

(21) Appl. No.: 13/057,837

(22) PCT Filed: Aug. 1, 2009

(86) PCT No.: PCT/DE2009/001093
§ 371 (c)(1),
(2), (4) Date: Feb. 7, 2011

(87) PCT Pub. No.: WO2010/017805
PCT Pub. Date: Feb. 18, 2010

(65) Prior Publication Data
US 2011/0138925 A1     Jun. 16, 2011

(30) Foreign Application Priority Data
Aug. 14, 2008     (DE) .................. 10 2008 037 760

(51) Int. Cl.
*G01N 3/00*     (2006.01)
*G01N 3/24*     (2006.01)

(52) U.S. Cl.
USPC .................. 73/788; 73/760; 73/841; 73/843

(58) Field of Classification Search
USPC ...................... 73/781, 862.08, 843
See application file for complete search history.

(56) References Cited

U.S. PATENT DOCUMENTS

| | | | | |
|---|---|---|---|---|
| 3,763,698 A | | 10/1973 | Suzuki et al. | |
| 4,036,080 A | * | 7/1977 | Friedericy et al. | ......... 74/572.11 |
| 4,927,407 A | * | 5/1990 | Dorman | ......... 600/16 |
| 4,977,794 A | * | 12/1990 | Metcalf | ......... 482/63 |
| 5,028,807 A | * | 7/1991 | Kawai et al. | ......... 307/119 |
| 6,615,670 B2 | * | 9/2003 | Shibasaki et al. | ......... 73/781 |
| 6,820,503 B2 | * | 11/2004 | Sueyoshi et al. | ......... 73/862.08 |
| 2003/0062304 A1 | | 4/2003 | Sueyoshi et al. | |

OTHER PUBLICATIONS

Maziere, M., 2006. Overspeed burst of turboengine disks. PhD thesis. Mines Paris-ParisTech.*
Maziere, M. et al., "Overspeed burst of elastoviscoplastic rotating disks: Part II—Burse of a superalloy turbine disk" European Journal of Mechanics A/Solids, 28 (2009) pp. 428-432.
Gayda, J. and Kantzos, P., Cyclic Spin Testing of Superalloy Disks With a Dual Grain Microstructure, NASA/TM-2005-213810.
Wang, W., "Disk Crack Detection and Diagnosis for Gas Turbine Engines", Aerospace Conference, 2006 IEEE Big Sky, MT, USA Mar. 4-11, 2006.

* cited by examiner

*Primary Examiner* — Leonard Chang
*Assistant Examiner* — Irving A Campbell
(74) *Attorney, Agent, or Firm* — Barlow, Josephs & Holmes, Ltd.

(57) ABSTRACT

Described is a material sample for testing material properties under biaxial load as well as a method therefor. The material sample has a circular disk shape and, for rotation about the center line thereof, is provided with an integrally formed hub. The edge of the material sample and the hub are thicker than the ring section of the material sample located in between. In one embodiment, the ring section is designed with an annular concave fillet concentric to the hub and the concave fillet may extend from the edge to the hub and have a continuous curvature over its width. In the method, it is rotated about its center line at least at 100,000 rpm, preferably at 150,000 rpm±10,000 rpm.

11 Claims, 2 Drawing Sheets

MATERIAL SAMPLE FOR TESTING BIAXIAL STRESS CONDITIONS

BACKGROUND OF THE INVENTION

The invention relates to a material sample for carrying out material tests under biaxial stress conditions as well as to a material sample setup and a material sample testing machine in which the material sample finds use.

During the design and sizing of machine components and the calculation of the strength of the components, the typical material strength values of the materials are resorted to in order to keep the amount of material used in the component as small as possible and nonetheless to fulfill the requirements placed on the components.

Especially when expensive materials are used and in light-weight construction, there is still potential for further saving of material and/or reducing weight when the actual material properties are known precisely.

In many fields of technical application, materials are used not only in their pure form, but oftentimes the surfaces of the components are furnished with engineered surface coatings, which impart specific desired surface properties to the component, although they usually change the strength values, especially in the case of narrow or thin components. The processing of materials also exerts an influence on the strength values.

In addition, the strength values of homogeneous materials may also be direction-dependent.

In order to be able to truly exploit the potential saving lying in a precise dimensioning, it is thus necessary again and again to determine appropriately the strength values of materials in the individual case. A biaxial stress distribution, as also arises in reality, is used in order to take into account the directional dependence of the strength values in the testing method.

Figure 2:
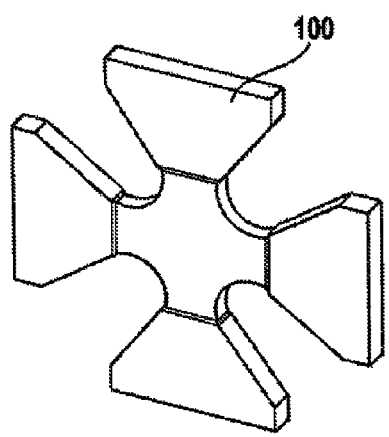

The prior art, for example, is the biaxial tensile test based on a so-called cross sample 100, as is shown in FIG. 2. A cross-shaped test piece 100 is produced from the material that is to be tested and is then placed under tension at the crossbars in an appropriate tensile testing machine. The desired characteristic values of the material are determined from the deformation/breakage of the sample. These samples are relatively complicated; conventional cross samples made of expensive material that is to be investigated have a span width of 270 mm with a thickness of 15 mm and weigh about 4 kg (titanium).

Figure 3:
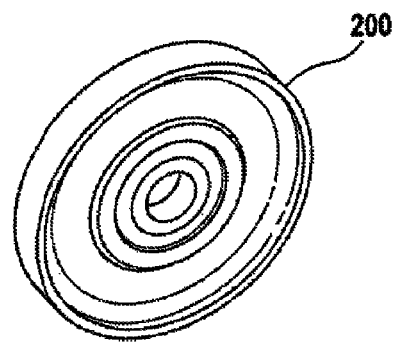

In order to generate a more uniform biaxial stress load in the material in departure from the classical tensile test, which is limited to two predetermined axes, centrifugal tests using model disks 200, as are shown in FIG. 3, are carried out at speeds of around 50,000 rpm. This enables the required strength determination of the disks to be obtained or else it is possible to determine the desired characteristic values of the material from changes in shape or breakage resulting from the forces arising in the disk. These test pieces are also complicated and expensive; designed disks have diameters of 220 mm and weigh about 3 kg (titanium). In addition, it is necessary here to include mounting steps in order, for example, to attach the disk to be tested to a hub, etc., before it can be tested.

BRIEF SUMMARY OF THE INVENTION

In contrast to this, the invention is based on the problem of proposing a material sample and a testing method working therewith by means of which it is possible to record biaxial material data quickly, inexpensively and precisely.

In regard to the material sample, the problem is solved by a material sample and method according to the present invention.

Provided in accordance with the invention is a material sample, which has a circular disk shape and, for rotation about its center line, has an integrally formed hub, for testing material properties under biaxial load, with the edge of the material sample and the hub being thicker than the ring section of the material sample located in between. This material sample can be fabricated as one piece and can be counterbalanced with little effort in order to be able to withstand the high speeds of approximately 150,000 rotations per minute.

Preferably, the ring section has an annular concave fillet concentric to the hub, and this fillet may extend from the hub to the edge and may have a continuous curvature over its width. A condition of high biaxial stresses in the sample is achieved through this design shape.

In advantageous embodiments of the invention, the curvature may be a circular arc or else an elliptical section. Preferably, the ring section and the edge of the disk-shaped material sample are symmetrical with respect to the center plane thereof.

For coupling the material sample to a rotary drive, the hub may have a stay bolt, which extends from the hub center concentrically to the center line of the material sample; however, it can also have a threaded bore, which extends concentrically to the center line into the material sample.

Proposed in accordance with the invention is, in addition, a method for testing material properties under biaxial load, in which a material sample, which has a circular disk shape and, for rotation about its center line, has an integrally formed hub, with the edge of the material sample and the hub being thicker than the ring section of the material sample located in between, is rotated about its center line at least at 100,000 rpm.

Preferably, the speed during the testing is 150,000 rpm±10,000 rpm.

BRIEF DESCRIPTION OF THE SEVERAL VIEWS OF THE DRAWINGS(S)

Figure 1:
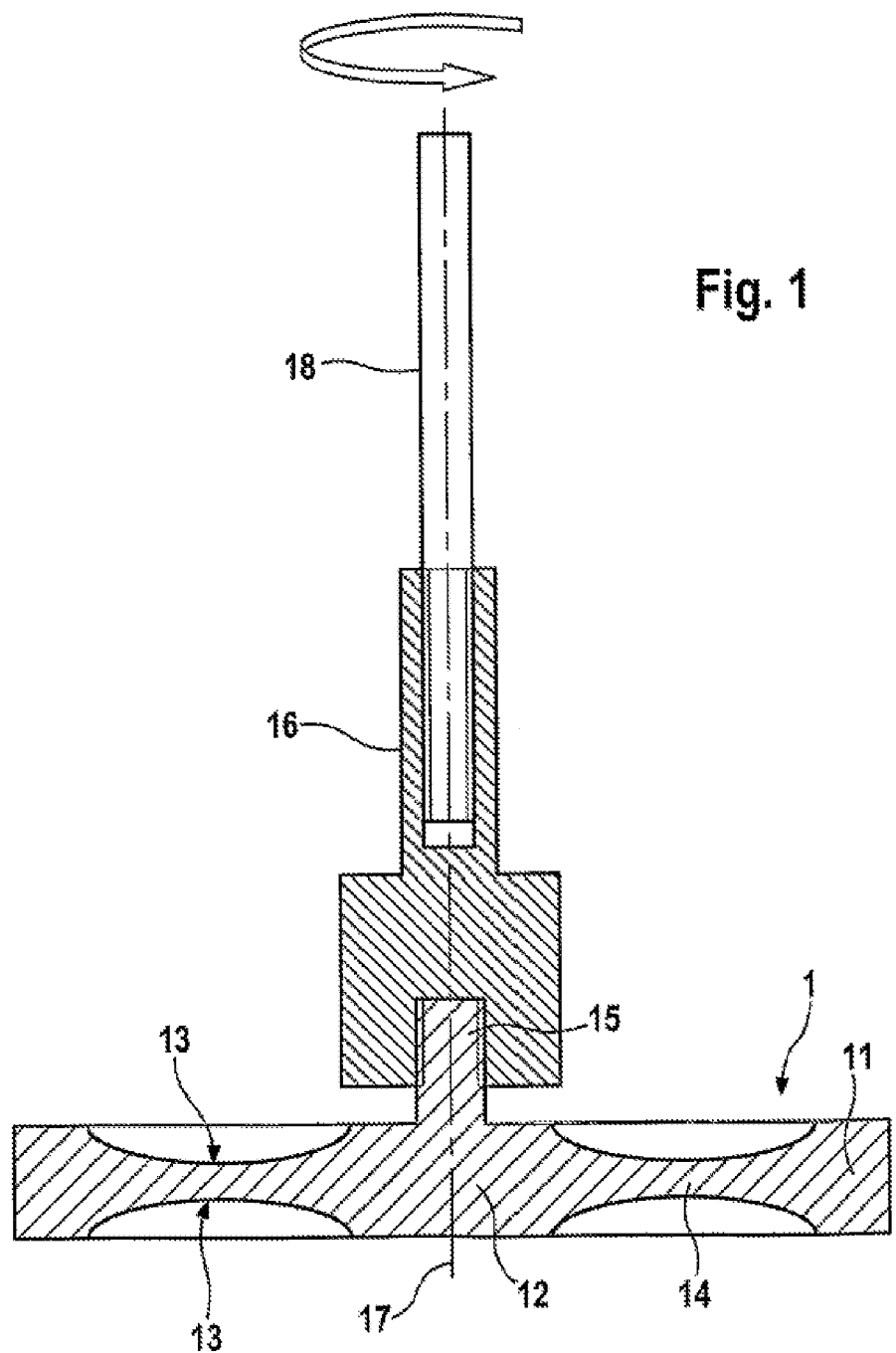

The invention will be described below in greater detail on the basis of a preferred exemplary embodiment with reference to the drawing. Herein is shown:

FIG. 1, a schematic sectional view of an exemplary embodiment of a material sample, which is inserted into a testing machine;

FIG. 2, a cross sample according to the prior art; and

FIG. 3, a centrifugal disk according to the prior art.

DETAILED DESCRIPTION OF THE INVENTION

According to FIG. 1, a material sample 1 has a disk shape and is rotationally symmetric with respect to a center line 17. The material sample 1 comprises a hub 12, an edge 11, and a ring section 14, which extends between edge 11 and hub 12. A stay bolt 15 stands on the hub 12 and extends concentrically to the center line 17. In the embodiment shown, edge 11, ring section 14, hub 12, and stay bolt 15 are designed as a single piece; that is, they are fabricated from one piece of material. This is often also referred to as single-piece fabrication. In this way, the material properties are not changed by joining methods or the like. In departure from this design, the stay bolt may be replaced by a bore with or without a thread, in which a suitable pin or bolt can be inserted.

In the present example, the curvature of the concave fillet 13, which extends over the entire ring section 14 of the material sample 1, has the cross-sectional shape of a curve that may be referred to as an elliptical section. However, it is also possible to choose other cross-sectional shapes for the concave fillet 13. In this way, it is possible to influence the stress distribution arising in the sample 1 during the test.

The material sample 1 is joined by means of a stay bolt 15 to an arbor 16, which has two concentric threaded bores of different diameter, into which the stay bolt 15, on the one end, and a drive shaft 18 of the testing machine (not further illustrated here), on the other end, are screwed. This joining technique allows sample 1 to be switched out relatively fast and simply. This saves time and money during the tests.

The material sample described in FIG. 1 is also, however, markedly smaller and lighter than the conventional centrifugal disks described at the beginning, so that the fastening to the hub by means of a simple screw connection offers an adequate strength. In addition, the quantity of material saved is substantial. This is shown as follows by a few numbers for the embodiment shown in FIG. 1: diameter 76 mm; thickness at the edge 8 mm; weight 96 g.

The arbor has a diameter of 20 mm and 9 mm and the drive shaft has a diameter of only 4 mm.

In general, it can be stated that designs of the material sample with the following dimensional ranges fulfill their purpose: diameter of 50 mm to 100 mm, in particular 76 mm±5 mm; thickness at the edge of 8 mm±2 mm; smallest thickness at the ring section of 3 mm±2 mm.

When the material sample 1 shown in FIG. 1 undergoes the method for testing material properties under biaxial load, it is fixed in place in the testing machine; that is, stay bolt 15 and drive shaft 18 are joined to one another in a rotationally rigid manner through the arbor 16. The material sample 1 is then rotated at least at 100,000 rpm, preferably at 150,000 rpm±10,000 rpm.

From the deformation or from the speed of rotation at breakage of the material sample, it is possible to deduce the strength values that are being sought.

For reasons of completeness, it is mentioned that material sample 1 may be specially designed or may be furnished with engineered surface coatings (not illustrated), so that, from comparative tests using coated and uncoated or differently coated material samples, it is possible to draw conclusions about the influence of the surface coatings or surface designs.

The following materials, among others, come into consideration as materials:
Material sample: Ti6246 or DA718
Arbor: 42CrMoV4 or IN718

In summary, the following advantages can be obtained using the technical teaching in accordance with the invention:
Possibility of determining biaxial material data on samples having technically relevant surfaces;
Low use of material;
Markedly reduced production costs, testing costs, testing times;
High testing volume in comparison to laboratory material samples;
Surface properties and shape are comparable to those of a real disk.

The invention claimed is:

1. A material sample (1) for testing material properties under biaxial load under rotation about its center line (17), with the material sample (1) having a circular disk shape and having a hub (12), a ring section (14), and an edge (11), with the edge (11) and the hub (12) being axially thicker than the ring section (14) located in between, with the ring section (14) being designed with a concave fillet (13) that is concentric to the center line (17) on the two respective sides of the material sample (1) and that extends from the hub (12) to the edge (11) and is curved at least in sections over its width, a rotating stay bolt (15) integrally connected to and extending from the hub (12) concentrically to the centerline (17) of the material sample (1) whereby the stay bolt (15) rotates with the hub, wherein the material sample (1) is a solid disk without a through-going centric hub bore, completely rotationally symmetric, or at least predominantly symmetric; the material sample being configured and arranged to rotate about the center line, and wherein the stay bolt (15), hub (12), ring section (14), and edge (11) are integrally formed from the same material into a unitary member.

2. The material sample according to claim 1, wherein the curvature of the concave fillet (13) is an elliptical section.

3. The material sample according to claim 1, wherein the ring section (14) and the edge (11) of the disk-shaped material sample (1) are symmetric with respect to their center plane.

4. The material sample according to claim 1, wherein the material sample (1) has a diameter of 50 mm to 100 mm.

5. The material sample according to claim 1, wherein the material sample (1) has a diameter of 76 mm±5 mm.

6. The material sample according to claim 1, wherein the edge (11) of the material sample (1) has a thickness of 8 mm±2 mm.

7. The material sample according to claim 1, wherein the ring section (14) of the material sample (1) has a minimum thickness of 3 mm±2 mm.

8. A material testing setup for testing materials under biaxial load, having a material sample (1) according to claim 1 and an arbor (16), which is joined to the stay bolt (15) of the hub (12).

9. A material testing machine for testing materials under biaxial load, having
a material testing setup according to claim 8 and
a drive device having a drive shaft (18) that can be coupled to the arbor (16).

10. The material testing machine according to claim 9, wherein the drive device is designed to rotate drive shaft (18), together with the material sample (1) coupled thereto at over 100,000 rpm.

11. A method for testing material properties under biaxial load, comprising the steps of:
providing a material sample that has a circular disk shape and, for rotation about its center line, has a hub, a stay bolt integrally connected to the hub that rotates with the hub, a ring section, and an edge, wherein the edge of the material sample and the hub are thicker than the ring section of the material sample located in between, and wherein the material sample is a solid disk, and wherein the stay bolt, hub, ring section, and edge are integrally formed from the same material into a unitary member; and
rotating the material sample about its center line at least at 100,000 rpm.

* * * * *